US005843688A

United States Patent [19]

Wölfel et al.

[11] Patent Number: 5,843,688

[45] Date of Patent: Dec. 1, 1998

[54] ISOLATED TYROSINASE DERIVED PEPTIDES AND USES THEREOF

[75] Inventors: Thomas Wölfel, Mainz, Germany; Aline Van Pel, Brussels, Belgium; Vincent Brichard, Brussels, Belgium; Thierry Boon-Falleur, Brussels, Belgium; Etienne DePlaen, Brussels, Belgium; Pierre Coulie, Brussels, Belgium; Jean-Christophe Renauld, Brussels, Belgium; Bernard Lethe, Brussels, Belgium

[73] Assignee: Ludwig Institute For Cancer Research, New York, N.Y.

[21] Appl. No.: 583,238

[22] Filed: Jan. 5, 1996

Related U.S. Application Data

[60] Division of Ser. No. 203,054, Feb. 28, 1994, which is a continuation-in-part of Ser. No. 81,673, Jun. 23, 1993, Pat. No. 5,487,974, which is a continuation-in-part of Ser. No. 54,714, Apr. 28, 1993, abandoned, which is a continuation of Ser. No. 994,928, Dec. 22, 1992.

[51] Int. Cl.$^{6}$ ........................ G01N 33/53; A61K 39/385; A61K 38/04

[52] U.S. Cl. ........................ 435/7.24; 424/193.1; 530/328

[58] Field of Search ........................ 435/7.24; 424/193.1; 530/328

[56] References Cited

U.S. PATENT DOCUMENTS 4,898,814 2/1990 Kwon .......................................... 435/6

OTHER PUBLICATIONS

Traversari et al., Transfection and expression of a gene coding for a human melanoma antigen recognized by autologous cytolytic T Lymphocytes, Immunogenetics 35: 145–152, Abstract, first sentence, p. 146, column 2, "CTL clones", p. 147, column 1. 1992.

Greenberg, Therapy of murine leukemia with cyclophosphamide and immune lyt–2+ cells: cytolytic T cells can mediate eradication of disseminated leukemia, J. Immunology, vol. 136, No. 5, p. 1917, column 2, 1st sentence of the 1st paragraph. Mar. 1986.

Ruppert et al., Multiple transcripts of the mouse tyrosinase gene are generated by alternative splicing, The EMBO J. vol. 7, No. 9, pp. 2715–2722, p. 2715, column 1, lines 5–7. Jun. 1988.

Brichard, et al, "The Tyrosinase Gene Codes for an Antigen Recognized by Autologous Cytolytic T Lymphocytes on HLA–A2 Melanomas", J. Exp. Med. 178: 489–495 (1993).

Coulie, et al, "Genes Coding For Tumor Antigens Recognized by Human Cytolytic T Lymphocytes", J. Immunotherapy 14: 104–109 (1993).

Slingluff, et al, "Recognition of Human Melanoma Cells by HLA–A2.1 Restricted Cytotoxic T Lymphocytes As Mediated By At Least Six Shared Peptide Epitopes", J. Immunol. 150(7): 2955–2963 (Apr. 1, 1993).

Barinaga, "Getting Some 'Backbone': How MHC Binds Peptides" Science 257: 880–881 (Aug. 14, 1992).

Wolfel, et al, "Lysis of Human Melanoma Cells by Autologous Cytolytic T Cells Clones", J. Exp. Med. 170: 797–810 (Sep. 1989).

*Primary Examiner*—Ponnathapura Achutamurthy
*Assistant Examiner*—Hankyel T. Park
*Attorney, Agent, or Firm*—Felfe & Lynch

[57] ABSTRACT

The invention relates to the identification of complexes of human leukocyte antigen molecules and tyrosinase derived peptides on the surfaces of abnormal cells. The therapeutic and diagnostic ramifications of this observation are the subject of the invention.

3 Claims, 11 Drawing Sheets

ISOLATED TYROSINASE DERIVED PEPTIDES AND USES THEREOF

RELATED APPLICATION

This application is a Divisional of Ser. No. 08/203,054 filed Feb. 28, 1994 which is a continuation-in-part of Ser. No. 08/081,673, filed Jun. 23, 1993, now U.S. Pat. No. 5,487,974, which is a continuation-in-part of Ser. No. 054, 714 filed Apr. 28, 1993, now abandoned, which is a continuation of Ser. No. 994,928 filed Dec. 22, 1992.

FIELD OF THE INVENTION

This invention relates to isolated peptides, derived from tyrosinase which are presented by HLA-A2 molecules and uses thereof. In addition, it relates to the ability to identify those individuals diagnosed with conditions characterized by cellular abnormalities whose abnormal cells present complexes of these peptides and HLA-A2, the presented peptides, and the ramifications thereof.

BACKGROUND AND PRIOR ART

The process by which the mammalian immune system recognizes and reacts to foreign or alien materials is a complex one. An important facet of the system is the T cell response. This response requires that T cells recognize and interact with complexes of cell surface molecules, referred to as human leukocyte antigens ("HLA"), or major histocompatibility complexes ("MHCs"), and peptides. The peptides are derived from larger molecules which are processed by the cells which also present the HLA/MHC molecule. See in this regard Male et al., *Advanced Immunology* (J. P. Lipincott Company, 1987), especially chapters 6–10. The interaction of T cell and complexes of HLA/peptide is restricted, requiring a T cell specific for a particular combination of an HLA molecule and a peptide. If a specific T cell is not present, there is no T cell response even if its partner complex is present. Similarly, there is no response if the specific complex is absent, but the T cell is present. This mechanism is involved in the immune system's response to foreign materials, in autoimmune pathologies, and in responses to cellular abnormalities. Recently, much work has focused on the mechanisms by which proteins are processed into the HLA binding peptides. See, in this regard, Barinaga, Science 257: 880 (1992); Fremont et al., Science 257: 919 (1992); Matsumura et al., Science 257: 927 (1992); Latron et al., Science 257: 964 (1992).

The mechanism by which T cells recognize cellular abnormalities has also been implicated in cancer. For example, in PCT application PCT/US92/04354, filed May 22, 1992, published on Nov. 26, 1992, and incorporated by reference, a family of genes is disclosed, which are processed into peptides which, in turn, are expressed on cell surfaces, which can lead to lysis of the tumor cells by specific CTLs. The genes are said to code for "tumor rejection antigen precursors" or "TRAP" molecules, and the peptides derived therefrom are referred to as "tumor rejection antigens" or "TRAs". See Traversari et al., Immunogenetics 35: 145 (1992); van der Bruggen et al., Science 254: 1643 (1991), for further information on this family of genes.

In U.S. patent application Ser. No. 938,334, the disclosure of which is incorporated by reference, nonapeptides are taught which bind to the HLA-A1 molecule. The reference teaches that given the known specificity of particular peptides for particular HLA molecules, one should expect a particular peptide to bind one HLA molecule, but not others. This is important, because different individuals possess different HLA phenotypes. As a result, while identification of a particular peptide as being a partner for a specific HLA molecule has diagnostic and therapeutic ramifications, these are only relevant for individuals with that particular HLA phenotype. There is a need for further work in the area, because cellular abnormalities are not restricted to one particular HLA phenotype, and targeted therapy requires some knowledge of the phenotype of the abnormal cells at issue.

The enzyme tyrosinase catalyzes the reaction converting tyrosine to dehydroxyphenylalanine or "DOPA" and appears to be expressed selectively in melanocytes (Muller et al., EMBOJ 7: 2715 (1988)). An early report of cDNA for the human enzyme is found in Kwon, U.S. Pat. No. 4,898,814. A later report by Bouchard et al., J. Exp. Med. 169: 2029 (1989) presents a slightly different sequence. A great deal of effort has gone into identifying inhibitors for this enzyme, as it has been implicated in pigmentation diseases. Some examples of this literature include Jinbow, WO9116302; Mishima et al., U.S. Pat. No. 5,077,059, and Nazzaropor, U.S. Pat. No. 4,818,768. The artisan will be familiar with other references which teach similar materials.

U.S. patent application Ser. No. 08/081,673, now U.S. Pat. No. 5,487,974, filed Jun. 23, 1993 and incorporated by reference, teaches that tyrosinase may be treated in a manner similar to a foreign antigen or a TRAP molecule—i.e., it was found that in certain cellular abnormalities, such as melanoma, tyrosinase is processed and a peptide derived therefrom forms a complex with HLA molecules on certain abnormal cells. These complexes were found to be recognized by cytolytic T cells ("CTLs"), which then lyse the presenting cells. The ramifications of this surprising and unexpected phenomenon were discussed. Additional peptides have now been found which also act as tumor rejection antigens presented by HLA-A2 molecules.

BRIEF DESCRIPTION OF THE FIGURES

FIG. 1A-1 shows lysis of cell lines LB24-MEL, by CTL IVSB;

FIG. 1B-1 shows lysis of cell line SK29-MEL, by CTL IVSB;

FIG. 1C-1 shows lysis of cell line LB4.MEL, by CTL IVSB;

FIG. 1D-1 shows lysis of cell line SK23.MEL, by CTL IVSB;

FIG. 1E-1 shows lysis of cell line LE516.MEL, by CTL IVSB;

FIG. 1F-1 shows lysis of cell line SK29-MEL.1.22 which has lost HLA-A2 expression, by CTL IVSB;

FIG. 1G-1 shows lack of lysis of MZ2-MEL, by CTL IVSB;

FIG. 1H-1 shows lysis of the loss variant in FIGS. 1F and 1F' after transfection with a gene for HLA-A2, by CTL IVSB;

FIG. 1I-1 shows lysis of the loss variant in FIGS. 1F and 1F' after transfection with a gene for HLA-A2, by CTL IVSB.

FIG. 7 shows, collectively, a series of chromium release assays using peptides described in this application on three different cell lines.

In FIG. 7, the symbol "○" is used for cell line T2, "■" for MZ2-MEL not presenting HLA-A2, and "●" for MZ2-MEL which has been transfected to present HLA-A2. Example 12 elaborates on these tests.

DETAILED DESCRIPTION OF PREFERRED EMBODIMENTS

EXAMPLE 1

Melanoma cell lines SK 29-MEL (also referred to in the literature as SK MEL-29) and LB24-MEL, which have been available to researchers for many years, were used in the following experiments.

Samples containing mononuclear blood cells were taken from patients SK29 (AV) and LB24 (these patients were also the source of SK 29-MEL and LB24-MEL, respectively). The melanoma cell lines were contacted to the mononuclear blood cell containing samples. The mixtures were observed for lysis of the melanoma cell lines, this lysis indicating that cytolytic T cells ("CTLs") specific for a complex of peptide and HLA molecule presented by the melanoma cells were present in the sample.

The lysis assay employed was a chromium release assay following Herin et al., Int. J. Cancer 39:390–396 (1987), the disclosure of which is incorporated by reference. The assay, however, is described herein. The target melanoma cells were grown in vitro, and then resuspended at $10^7$ cells/ml in DMEM, supplemented with 10 mM HEPES and 30% FCS, and incubated for 45 minutes at 37° C. with 200 $\mu$Ci/ml of $Na(^{51}Cr)O_4$. Labelled cells were washed three times with DMEM, supplemented with 10 mM Hepes. These were then resuspended in DMEM supplemented with 10 mM Hepes and 10% FCS, after which 100 ul aliquots containing $10^3$ cells, were distributed into 96 well microplates. Samples of PBLs were added in 100 ul of the same medium, and assays were carried out in duplicate. Plates were centrifuged for 4 minutes at 100 g, and incubated for four hours at 37° C. in a 5.5% of $CO_2$ atmosphere.

Plates were centrifuged again, and 100 ul aliquots of supernatant were collected and counted. Percentage of $^{51}$Cr release was calculated as follows:

$$\% \, ^{51}Cr \text{ release} = \frac{(ER-SR)}{(MR-SR)} \times 100$$

where ER is observed, experimental $^{51}$Cr release, SR is spontaneous release measured by incubating $10^3$ labeled cells in 200 ul of medium alone, and MR is maximum release, obtained by adding 100 ul 0.3% Triton X-100 to target cells.

Those mononuclear blood samples which showed high CTL activity were expanded and cloned via limiting dilution, and were screened again, using the same methodology.

The same method was used to test target K562 cells. When EBV-transformed B cells (EBV-B cells) were used, the only change was the replacement of DMEM medium by Hank's medium, supplemented with 5% FCS.

These experiments led to isolation of CTL clone "IVSB" from patient SK29 (AV) and CTL clone 210/9 from patient LB24.

Figures 1, 1A, 1B, 1C:
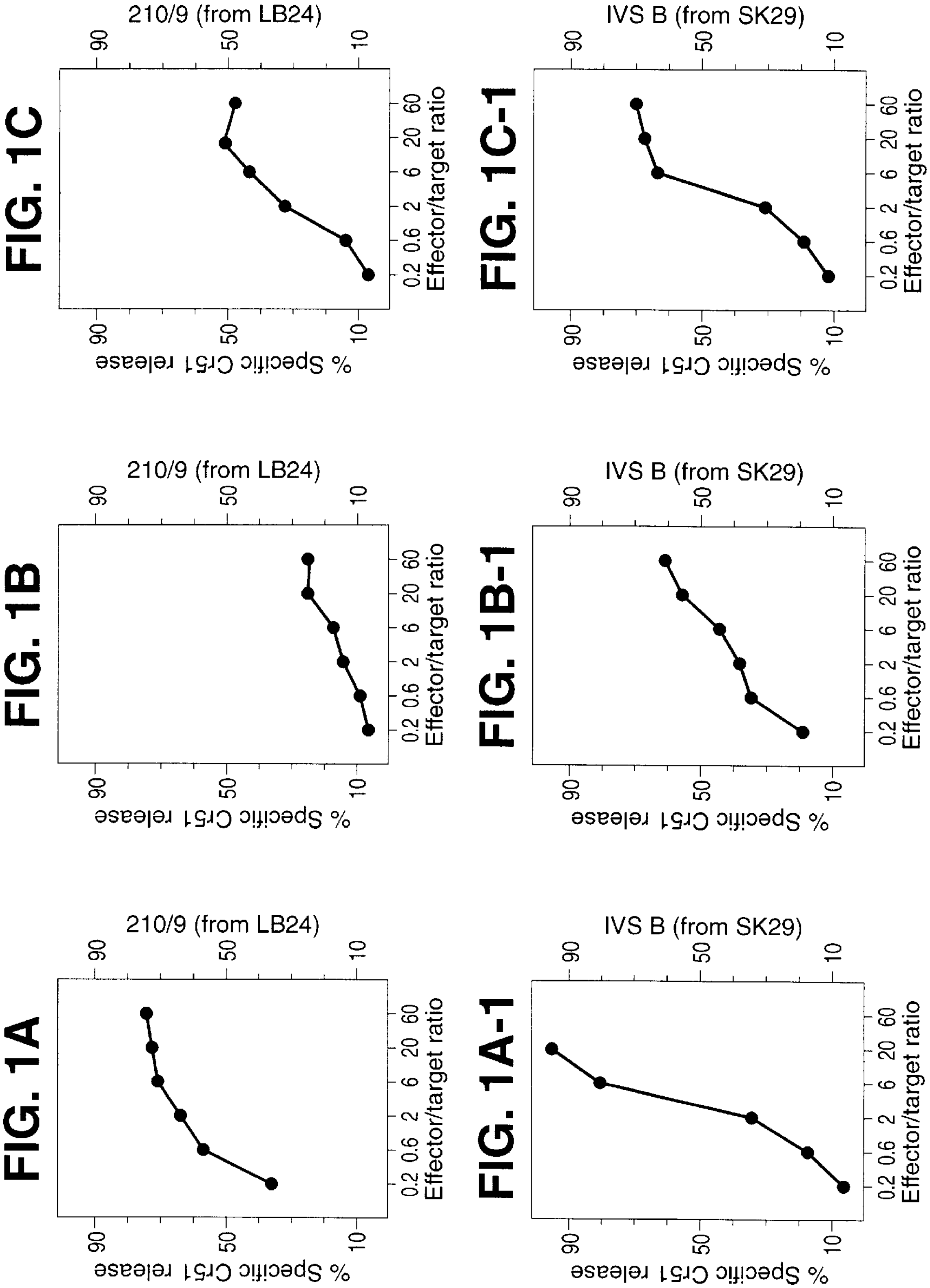
FIG. 1 describes, collectively, cell lysis studies. In particular.
FIG. 1A shows lysis of cell line LB24-MEL, by CTL 210/9.
FIG. 1B shows lysis of cell lines SK29-MEL, by CTL 210/9.
FIG. 1C shows lysis of cell line LB4.MEL, by CTL 210/9.
Figure 1E:
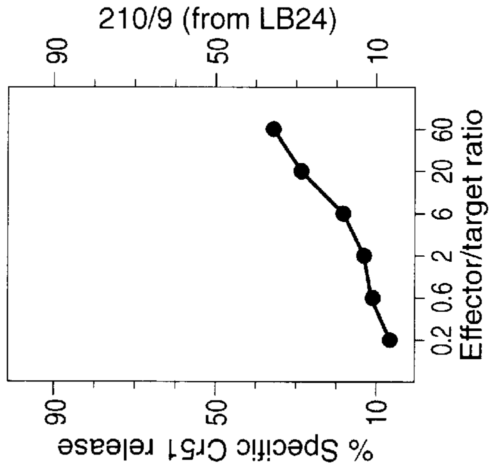
FIG. 1E shows lysis of cell line LE516.MEL, by CTL 210/9.
Figures 1, 1E:
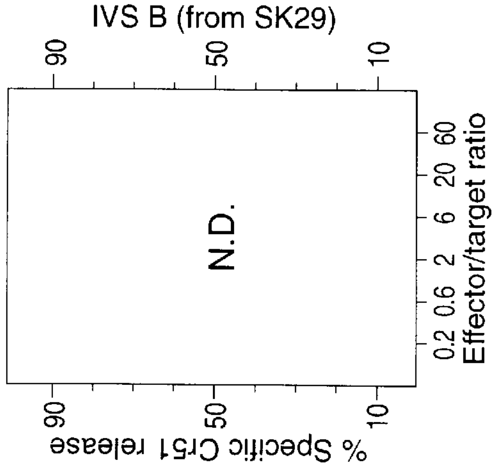
Figure 1D:
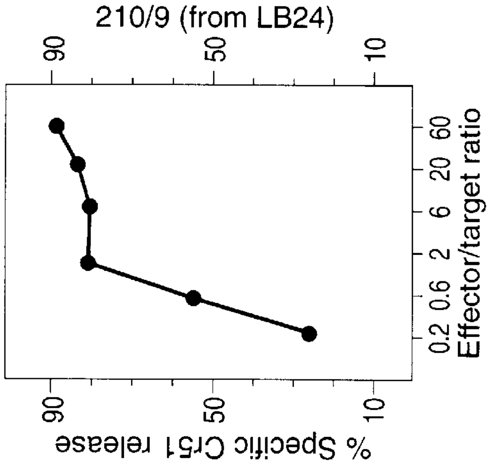
FIG. 1D shows lysis of cell line SK23.MEL, by CTL 210/9.
Figures 1, 1D:
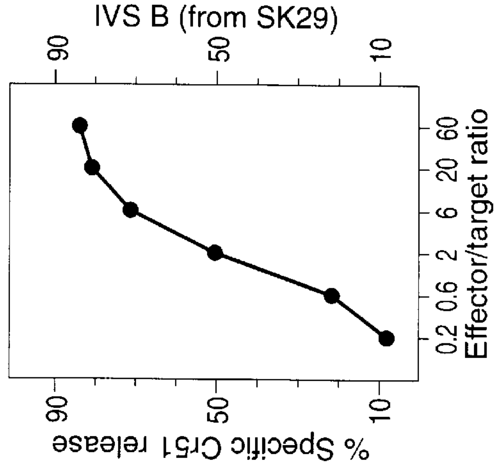
Figure 1F:
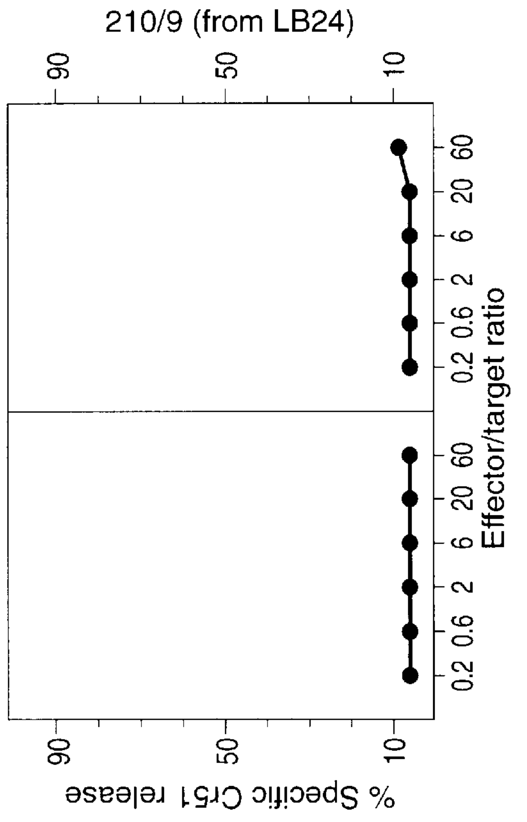
FIG. 1F shows lysis of cell line SK29-MEL.1.22 which has lost HLA-12 expression, by CTL 210/9.
Figures 1, 1F:
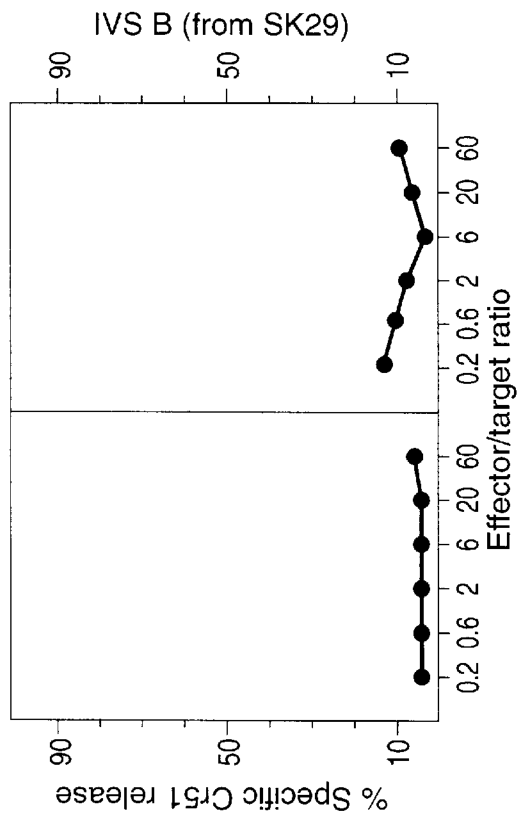
Figures 1, 1G, 1H, 1I:
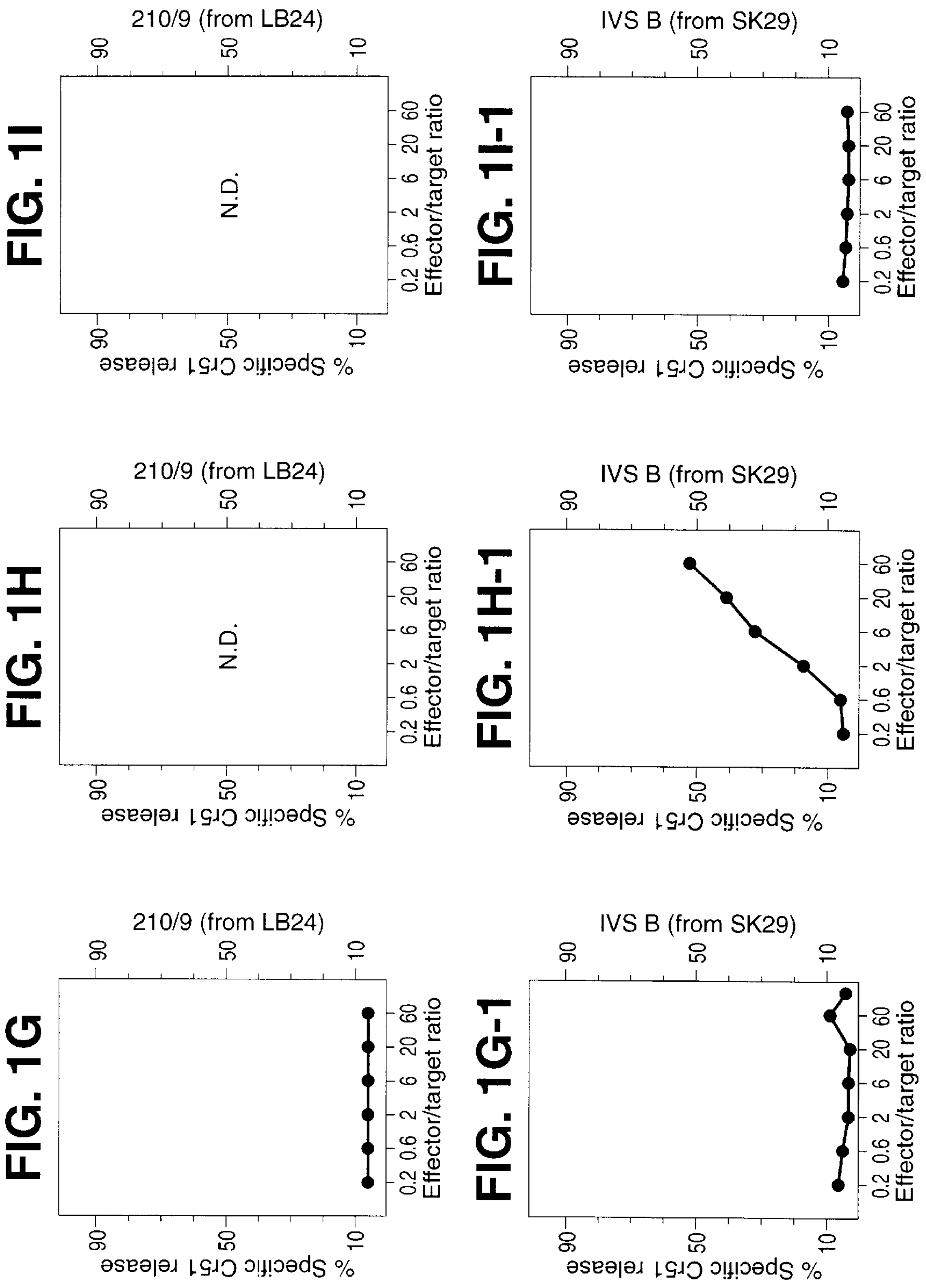
FIG. 1G shows lack of lysis of MZ2-MEL, by CTL 210/9.
FIG. 1H shows lysis of the loss variant in FIGS. 1F and 1F' after transfection with a gene for HLA-A2, by CTL 210/9.
FIG. 1I shows lysis of the loss variant in FIGS. 1F and 1F' after transfection with a gene for HLA-A2, by CTL 210/9.

FIG. 1 presents the results of these assays, in panels A, B, G and I. Specifically, it will be seen that both CTLs lysed both melanoma cell lines, and that there was no lysis of the K562 and EBVB cell lines.

EXAMPLE 2

The CTLs described were tested against other melanoma cell lines to determine whether their target was shared by other melanoma cell lines. Lysis as described in Example 1 was studied for lines LB4.MEL, SK23.MEL (also known as SK MEL-23), and LE516.MEL. FIG. 1, panels C, D and E shows that the clones did lyse these lines.

The tested lines are known to be of type HLA-A2, and the results suggested that the CTLs are specific for a complex of peptide and HLA-A2. This suggestion was verified by testing a variant of SK 29-MEL which has lost HLA-A2 expression. FIG. 1, panel F shows these results. Neither clone lysed the HLA-loss variant. When the variant was transfected with the HLA-A2 gene of SK29-MEL, however, and retested, lysis was observed. Thus, it can be concluded that the presenting molecule is HLA-A2.

EXAMPLE 3

Once the presenting HLA molecule was identified, studies were carried out to identify the molecule, referred to hereafter as the "tumor rejection antigen precursor" or "TRAP" molecule which was the source of the presented peptide.

To do this, total RNA was isolated from cell line SK29-MEL.1, which is a subclone of SK29-MEL. The RNA was isolated using an oligo-dT binding kit, following well recognized techniques. Once the total RNA was secured, it was transcribed into cDNA, again using standard methodologies. The cDNA was then ligated to EcoRI adaptors and cloned into the EcoRI site of plasmid pcDNA-I/Amp, in accordance with manufacturer's instructions. The recombinant plasmids were then electroporated into JM101 *E. coli* (electroporation conditions: 1 pulse at 25 $\mu$farads, 2500 V).

The transfected bacteria were selected with ampicillin (50 $\mu$g/ml), and then divided into 700 pools of 200 clones each. Each pool represented about 100 different cDNAs, as analysis showed that about 50% of plasmids contained an insert. Each pool was amplified to saturation, and plasmid DNA was isolated via alkaline lysis, potassium acetate precipitation and phenol extraction, following Maniatis et al., in Molecular Cloning: A Laboratory Manual (Cold Spring Harbor, N.Y., 1982). Cesium gradient centrifugation was not used.

EXAMPLE 4

The amplified plasmids were then transfected into eukaryotic cells. Samples of COS-7 cells were seeded, at 15,000 cells/well into tissue culture flat bottom microwells, in Dulbecco's modified Eagles Medium ("DMEM") supplemented with 10% fetal calf serum. The cells were incubated overnight at 37° C., medium was removed and then replaced by 30 μl/well of DMEM medium containing 10% Nu serum, 400 μg/ml DEAE-dextran, 100 μM chloroquine, 100 ng of plasmid pcDNA-I/Amp-A2 and 100 ng of DNA of a pool of the cDNA library described supra. Plasmid pcDNA-I/Amp-A2 contains the HLA-A2 gene from SK29-MEL. Following four hours of incubation at 37° C., the medium was removed, and replaced by 50 μl of PBS containing 10% DMSO. This medium was removed after two minutes and replaced by 200 μl of DMEM supplemented with 10% of FCS.

Following this change in medium, COS cells were incubated for 48 hours at 37° C. Medium was then discarded, and 2000 cells of either of the described CTL clones were added, in 100 μl of Iscove's medium containing 10% pooled human serum. When clone 210/9 was used, the medium was supplemented with 25 U/ml of IL-2. Supernatant was removed after 24 hours, and TNF content was determined in an assay on WEHI cells, as described by Traversari et al., Immunogenetics 35: 145–152 (1992), the disclosure of which is incorporated by reference.

Figure 2:
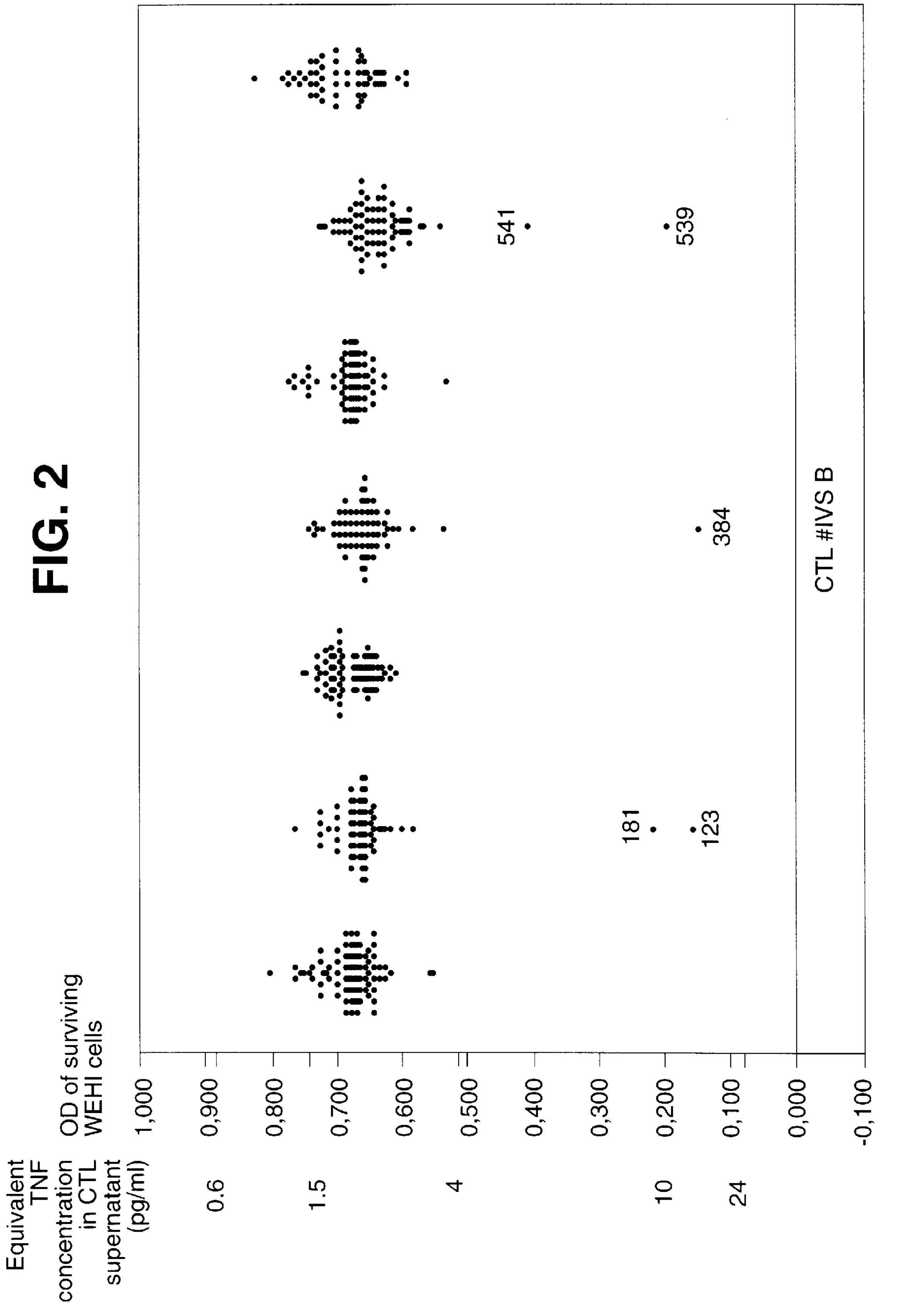
FIG. 2 presents studies of TNF release of CTL IVSB.
Figure 3:
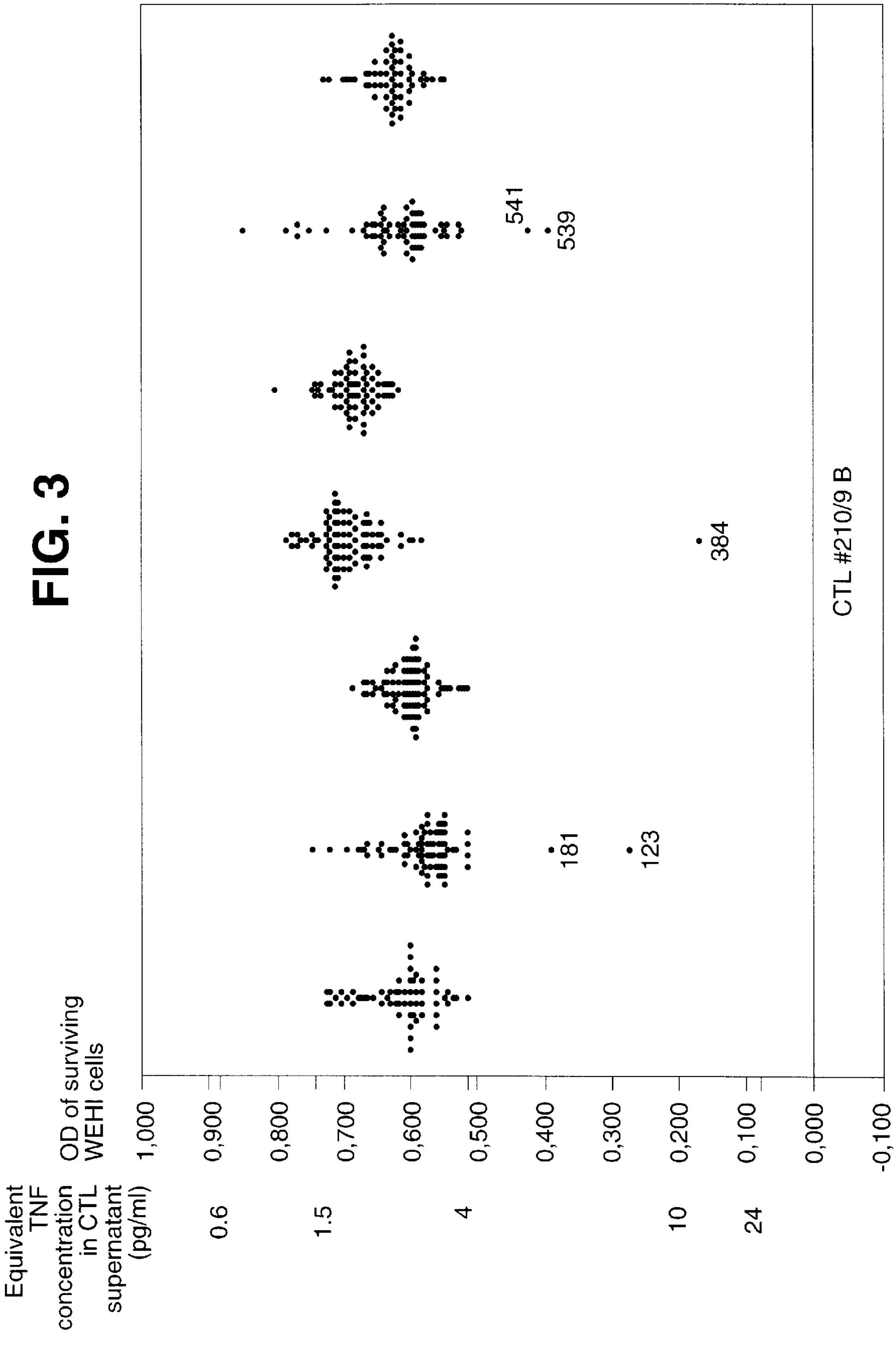
FIG. 3 depicts studies of TNF release of CTL 210/9.

Of 700 wells tested with IVSB, 696 showed between 0.6 and 4 pg of TNF per ml. The remaining four wells contained between 10 and 20 pg/ml of TNF. Homologous wells tested with CTL 210/9 showed similar, clearly higher values. FIGS. 2 and 3 present these data.

EXAMPLE 5

Three of the four pools identified as high producers (numbers "123", "181" and "384") were selected for further experiments. Specifically, the bacteria were cloned, and 570 bacteria were tested from each pool. Plasmid DNA was extracted therefrom, transfected into a new sample of COS cells in the same manner as described supra, and the cells were again tested for stimulation of CTL 210/9 and CTL IVSB. A positive clone was found in pool 123 ("p123.B2"), and one was found in pool 384 ("p384.C6"). Convincing evidence that the transfected cells were recognized by CTLs was obtained by carrying out a comparative test of COS cells transfected with cDNA and the HLA-A2 gene, and COS cells transfected only with HLA-A2. TNF release in CTL supernatant was measured by testing it on WEHI cells. The optical density of the surviving WEHI cells was measured using MTT. Results are presented in Table 1:

TABLE 1

| | cDNA (123.B2) + HLA-A2 DNA | no cDNA + HLA-A2 |
|---|---|---|
| Run 1 | 0.087 | 0.502 |
| Run 2 | 0.108 | 0.562 |

The values for WEHI OD's correspond to 24 pg/ml of TNF for cDNA and HLA-A2, versus 2.3 pg/ml for the control.

The plasmids from the positive clones were removed, and sequenced following art known techniques. A sequence search revealed that the plasmid insert was nearly identical to the cDNA for human tyrosinase, as described by Bouchard et al., J. Exp. Med. 169: 2029 (1989), the disclosure of which is incorporated by reference. Thus, a normally occurring molecule (i.e., tyrosinase), may act as a tumor rejection antigen precursor and be processed to form a peptide tumor rejection antigen which is presented on the surface of a cell, in combination with HLA-A2, thereby stimulating lysis by CTL clones. The nucleic sequence of the identified molecule is presented as SEQ ID NO: 1.

EXAMPLE 6

Prior work reported by Chomez et al., Immunogenetics 35: 241 (1992) has shown that small gene fragments which contain a sequence coding for an antigenic peptide resulted in expression of that peptide. This work, which is incorporated by reference in its entirety, suggested the cloning of small portions of the human tyrosinase cDNA described supra and in SEQ ID NO: 1. Using the methodologies described in examples 1–5, various fragments of the cDNA were cotransfected with a gene for HLA-A2 in COS-7 cells, and TNF release assays were performed. These experiments led to identification of an approximately 400 base pair fragment which, when used in cotransfection experiments, provoked TNF release from cytolytic T cell clone CTL IVSB discussed supra, shown to be specific for HLA-A2 presenting cells. The approximately 400 base fragment used corresponded to bases 711 to 1152 of SEQ ID NO: 1. The amino acid sequence for which the fragment codes was deduced, and this sequence was then compared to the information provided by Hunt et al., Science 255: 1261 (1992), and Falk et al., Nature 351: 290 (1991), the disclosures of which are both incorporated by reference in their entirety. These references discuss consensus sequences for HLA-A2 presented peptides. Specifically, Hunt discusses nonapeptides, where either Leu or Ile is always found at the second position, Leu being the "dominant residue". The ninth residue is described as always being a residue with an aliphatic hydrocarbon side chain. Val is the dominant residue at this position. Hunt discusses a strong signal for Leu and an intermediate signal for Met at the second position, one of Val, Leu, Ile or Thr at position 6, and Val or Leu at position 9, with Val being particularly strong. On the basis of the comparison, nonapeptides were synthesized and then tested to see if they could sensitize HLA-A2 presenting cells. To do so, tyrosinase loss variant cell lines SK29-MEL 1.218 and T202LB were used. Varying concentrations of the tested peptides were added to the cell lines, together with either of cytolytic T cell clone CTL IVSB or cytolytic T cell clone CTL 210/9. Prior work, described supra, had established that the former clone lysed tyrosinase expressing cells which present HLA-A2, and that the latter did not.

The tyrosinase loss variants were incubated for one hour in a solution containing $^{51}Cr$, at 37° C., either with or without anti HLA-A2 antibody MA2.1, which was used to stabilize empty HLA-A2 molecules. In the tests, cells were washed four times, and then incubated with varying dilutions of the peptides, from 100 μM down to 0.01 μM. After 30 minutes, effector cells were added at an E/T ratio of 40/1 and four hours later, 100λ of supernatant were collected and radioactivity counted.

Figure 4A:
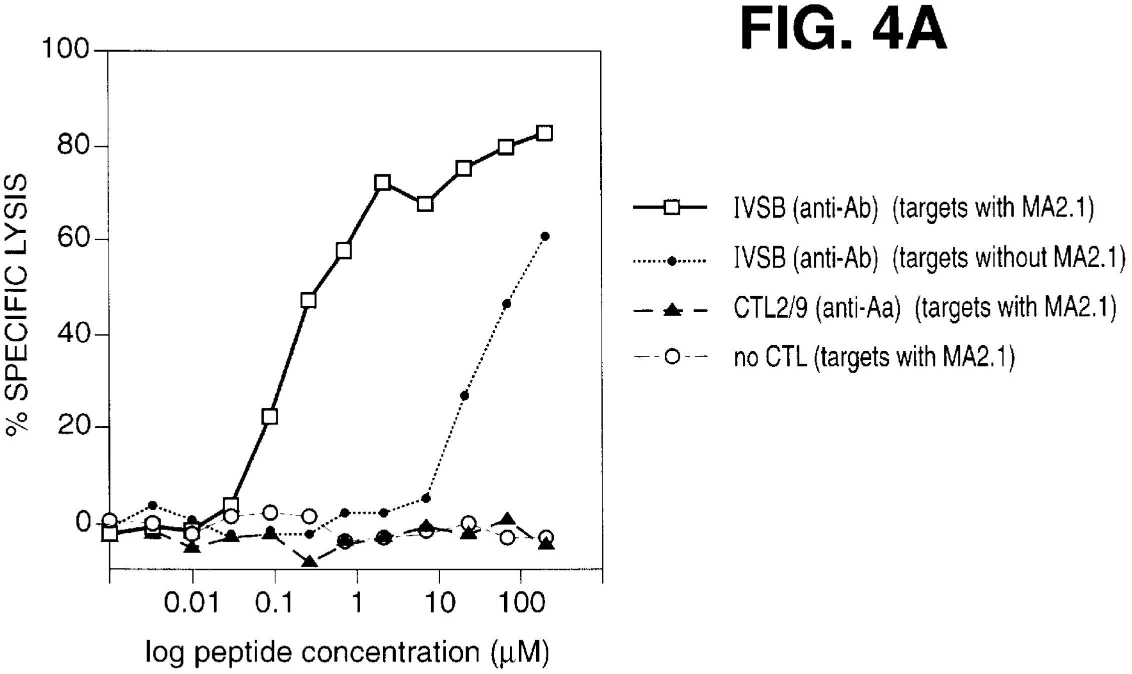
FIGS. 4A and 4B the recognition of the peptide SEQ ID NO: 2 by cytolytic T cell clone CTL-IVSB but not cytolytic T cell clone CTL 2/9.
Figure 4B:
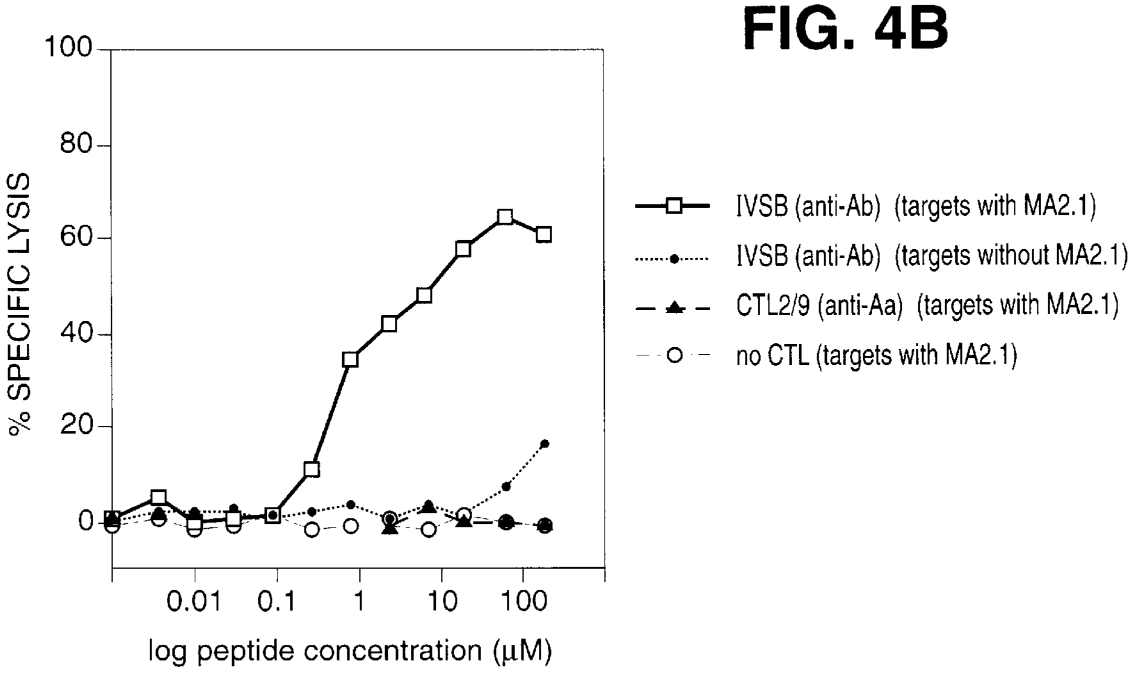
Figure 5:
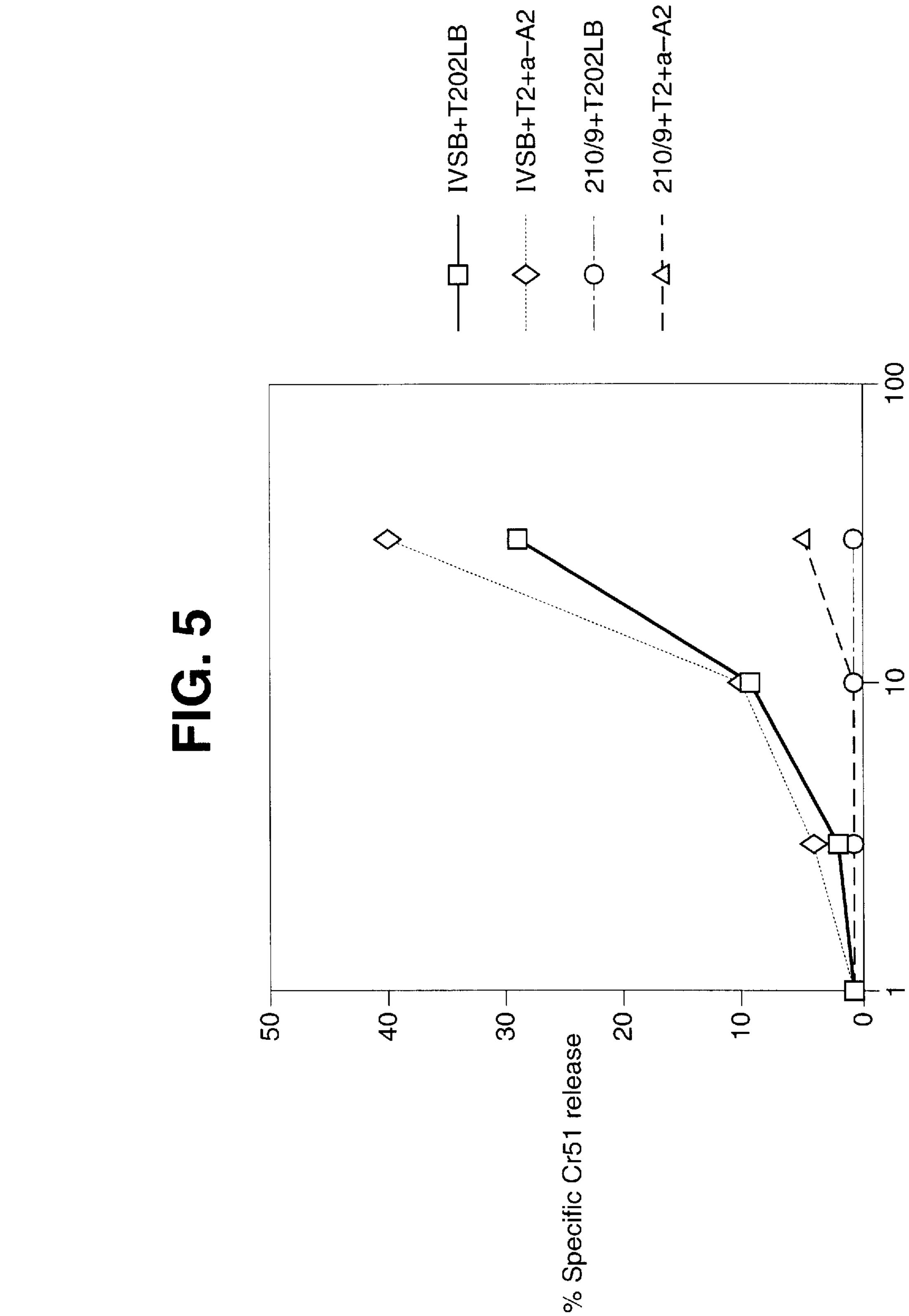
FIG. 5 shows that the peptide YMNGTMSQV is not recognized by cytolytic T cell clone CTL 210/9.

FIG. 4 shows the results obtained with nonapeptide

Tyr Met Asn Gly Thr Met Ser Gln Val.

(SEQ ID NO: 2).

This peptide, referred to hereafter as SEQ ID NO: 2, corresponds to residues 1129–1155 of the cDNA sequence for tyrosinase presented in SEQ ID NO: 1. Complexes of HLA-A2 and this peptide are recognized by CTL clone IVSB.

In a parallel experiment, it was shown that CTL clone CTL 210/9, derived from patient LB24, did not recognize the complexes of HLA-A2 and the peptide of SEQ ID NO:

2, although it did recognize complexes of HLA-A2 and a tyrosinase derived peptide. Thus, tyrosinase is processed to at least one additional peptide which, when presented by HLA-A2 molecules, is recognized by CTL clones.

EXAMPLE 7

In a follow-up experiment, a second gene fragment which did not encode the peptide of SEQ ID NO: 2 was used. This fragment began at base 1 and ended at base 1101 of SEQ ID NO: 1 (i.e. the EcoRI-SphI fragment). Cytolytic T cell clone CTL 210/9 discussed supra, was tested against COS-7 cells transfected with this fragment in the manner described supra. CTL IVSB was also tested. These results, showed that CTL 210/9 recognized an antigen on the surface of HLA-A2 expressing cells transfected with this fragment, but CTL IVSB did not. Thus, a second tumor rejection antigen peptide is derived from tyrosinase.

EXAMPLE 8

In order to further define the tumor rejection antigen recognized by CTL 210/9, the following experiments were carried out.

A second fragment, corresponding to bases 451–1158 of SEQ ID NO: 1 was transfected into COS cells together with a gene for HLA-A2, and TNF release assays were carried out. This sequence provoked TNF release from clone IVSB (20 pg/ml), but not from LB24-CTL 210/9 (3.8 pg/ml). These results confirmed that the two CTL clones recognize different peptides, and that the peptide recognized by CTL 210/9 must be encoded by region 1-451.

EXAMPLE 9

The tyrosinase derived peptide coded for by cDNA fragment 1-451 was analyzed for consensus sequences known to bind HLA-A2. The peptides corresponding to these consensus sequences were synthesized, and tested for their ability to sensitize HLA-A2 presenting cells. To do so, two tyrosinase negative melanoma cell lines were used (i.e., NA8-MEL, and MZ2-MEL 2.2 transfected with HLA-A2), and cell line T2, as described by Salter et al, Immunogenetics 21: 235–246 (1985)).

The cells were incubated with $^{51}Cr$, and monoclonal antibody MA2.1, which is specific for HLA-A2 for 50 minutes at 37° C., followed by washing (see Bodmer et al., Nature 342: 443–446 (1989), the disclosure of which is incorporated by reference in its entirety). Target cells were incubated with various concentrations of the peptides, and with either of LB 24-CTL clones 210/5 or 210/9. The percent of chromium release was measured after four hours of incubation.

The peptide Met Leu Leu Ala Val Leu Tyr Cys Leu Leu (SEQ ID NO: 3) was found to be active.

In further experiments summarized here, CTL-IVSB previously shown to recognize SEQ ID NO: 2, did not recognize the peptide of SEQ ID NO: 3.

The results are summarized in Tables 2–4 which follow:

TABLE 2

| | Peptide | |
|---|---|---|
| | SEQ ID NO: 2 | SEQ ID NO: 3 |
| CTL-IVSB | + | − |
| CTL-210/5 | − | + |
| CTL-210/9 | − | + |

TABLE 3

Lysis of MZ2-2.2.2 sensitized with tyrosinase peptides by CTL 210/5, CTL 210/9, and CTL IVSB

| Effectors | Peptides | Dose | MZ2.22.A2 + anti-A2 |
|---|---|---|---|
| CTL 210/5 | SEQ ID NO: 3 | 10 μM | 13 |
| (44:1) | | 1 | 17 |
| | SEQ ID NO: 2 | 30 μM | 16 |
| | | 10 | 1 |
| | | 3 | 1 |
| | | | 1 |
| | | 10 μm | 13 |
| | | 3 | 17 |
| CTL 210/9 | SEQ ID NO: 3 | 1 | 15 |
| (20:1) | SEQ ID NO: 2 | 30 M | 1 |
| | | 10 | 1 |
| | | 3 | 1 |
| | | 10 μM | 1 |
| CTL. IVSB | SEQ ID NO: 3 | 3 | 1 |
| (40:1) | | 1 | 1 |
| | SEQ ID NO: 2 | 30 μM | 63 |
| | | 10 | 63 |
| | | 3 | 62 |

*Target cells were incubated with $^{51}Cr$ and mono-Ab MA2.1 (anti-HLA-A2) for 50 minutes, then washed three times. They were incubated with various concentration of peptides for 30 min. CTL cells were added at the indicated (E:T) ratio. The % specific $^{51}Cr$ release was measured after 4 h incubation.

TABLE 4

Test of tyrosinase peptides recognized by LB24-CTL 210/3 and 210/9 or SK28-CTL IVSB

| | | | (% Cr51 specific release) | | |
|---|---|---|---|---|---|
| Effectors | Peptides | Dose | NA8-MEL* | MZ2-2.2: A2 | T2 |
| LB24-CTL | MILLAVLYCLL | 10 μM | 30 | 31 | 36 |
| 210/5 | (LAUS 17-5) | 3 | 23 | 27 | 35 |
| (41:1) | | 1 | 17 | 20 | 26 |
| | | 300 nM | 6 | 17 | 18 |
| | | 100 | 2 | 8 | 5 |
| | | 30 | 3 | 5 | 2 |
| | | 0 | 0 | 0 | 0 |
| LB24-CTL | MILAVLYCLL | 10 μM | 14 | 19 | 21 |
| 210/9 | (LAUS 17-5) | 3 | 13 | 17 | 20 |
| (28:1) | | 1 | 9 | 14 | 13 |
| | | 300 nM | 3 | 9 | 5 |

TABLE 4-continued

Test of tyrosinase peptides recognized by LB24-CTL 210/3 and 210/9 or SK28-CTL IVSB

| Effectors | Peptides | Dose | (% Cr51 specific release) NA8-MEL* | MZ2-2.2: A2 | T2 |
|---|---|---|---|---|---|
| | | 100 | 1 | 1 | 1 |
| | | 30 | 0 | 1 | 0 |
| | | 0 | 0 | 1 | 0 |
| SK29-CTL | YMNGTMSQV | 10 μM | 46 | 48 | 59 |
| IVSB | (MAINZ) | 3 | 38 | 44 | 52 |
| (42:1) | | 1 | 27 | 40 | 48 |
| | | 300 nM | 14 | 22 | 34 |
| | | 100 | 3 | 13 | 21 |
| | | 30 | 1 | 9 | 10 |
| | | 10 | 1 | 3 | 3 |
| | | 3 | 0 | 3 | 4 |
| | | 1 | 0 | 1 | 0 |
| | | 0 | 0 | 4 | 0 |
| spt. rel. | | | 339 | 259 | 198 |
| max-spt | | | 2694 | 1693 | 1208 |
| % | | | 11 | 13 | 14 |

EXAMPLE 10

Additional experiments were carried out using CTL clone 22/31. This clone had previously been shown to lyse subline MZ2-MEL.43 from autologous melanoma cell line MZ2-MEL, but did not lyse other sublines, such as MZ2-MEL 3.0 and MZ2-MEL 61.2, nor did it lyse autologous EBV transformed B cells, or killer cell line K562 (see Van den Eynde et al., Int. J. Cancer 44: 634–640 (1989)). The antigen presented by MZ2-MEL.43 is referred to as antigen C.

In prior work including that reported in the parent of this application, it was found that the tyrosinase gene encodes an antigen recognized by autologous CTLs on most HLA-A2 expressing melanomas. Expression of this gene in sublines of cell line MZ2-MEL was tested by PCR amplification. Clone MZ2-MEL.43 was found to be positive, whereas other MZ2-MEL clones, such as MZ2-MEL.3.0 were negative. Correlation of expression of the tyrosinase gene, and antigen MZ2-C, suggested that MZ2-C might be a tumor rejection antigen derived from tyrosinase, and presented by an HLA molecule expressed by MZ2-MEL. This cell line does not express HLA-A2, which would indicate that if a tyrosinase derived peptide were presented as a TRA, a second HLA molecule was implicated.

Figure 6:
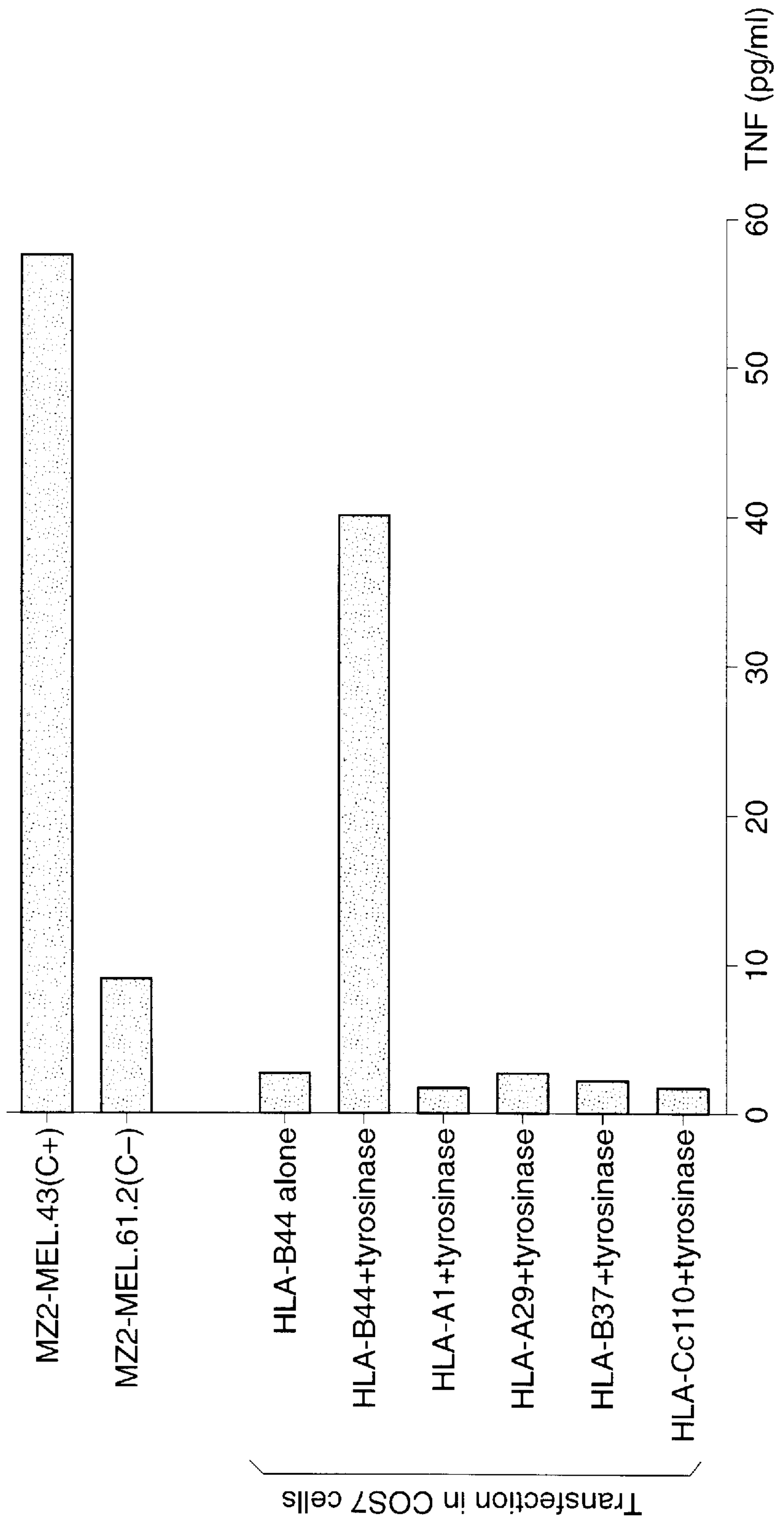
FIG. 6 shows the results obtained when TNF release assays were carried out on various cells, including those which present HLA-B44 on their surface.

Studies were carried out to identify which HLA molecule presented antigen C to CTL 22/31. To determine this, cDNA clones of the HLA molecules known to be on the cell surface, i.e., HLA-A29, HLA-B37, HLA-B 44.02, and HLA-C clone 10, were isolated from an MZ2-MEL.43 cDNA library, and then cloned into expression vector pcDNAI/Amp. Recipient COS 7 cells were then transfected with one of these constructs or a construct containing HLA-A1, plus cDNA coding for tyrosinase (SEQ ID NO: 1). The contransfection followed the method set forth above. One day later CTL 22/31 was added, and 24 hours later, TNF release was measured by testing cytotoxicity on WEHI-164-13, following Traversari et al, supra. FIG. 6 shows that TNF was released by CTL 22/31 only in the presence of cells transfected with both HLA-B44 and tyrosinase. The conclusion to be drawn from this is that HLA-B44 presents a tyrosinase derived tumor rejection antigen.

EXAMPLE 11

The experiments described supra showed, inter alia, that the decamer of SEQ ID NO: 3 effectively induced lysis of HLA-A2 presenting cells. It is fairly well accepted that MHC molecules present nonapeptides. To that end, experiments were carried out wherein two nonamers were tested, which were based upon the decapeptide which did give positive results.. Specifically, either the first or tenth amino acid was omitted to create two peptides, i.e.:

Met Leu Leu Ala Val Leu Tyr Cys Leu (SEQ ID NO: 4)

Leu Leu Ala Val Leu Tyr Cys Leu Leu (SEQ ID NO: 5).

These peptides were tested in the same way the decapeptide was tested, as set forth in the prior examples at concentrations ranging from 10 μM to 1 nM. Three presenting cells were used. As summarized in Table 5, which follows, "T2" is a mutant human cell line, "CEMX721.174T2" as described by Salter, Immunogenetics 21: 235 (1985). This line presents HLA-A2. "G2.2" is a variant of the cell line MZ2-MEL. The variant has been transfected with a gene coding for HLA-A2. The abbreviation "G2.2.5" stands for a variant which does not express HLA-A2. All cells were incubated with monoclonal antibody MA2.1 prior to contact with the cytolytic T cell clone. This procedure stabilizes so-called "empty" MHC molecules, although the mechanism by which this occurs is not well understood and effector CTLs 210/5 and 210/9 were both used. The results are set forth in Table 5, which follows. They show that at a concentration of 10 μM, the nonamer of SEQ ID NO: 4 was twice as effective when used with CTL clone 210/5, and four times as effective with clone 210/9 whereas the nonamer of SEQ ID NO: 5 was ineffective at inducing lysis.

EXAMPLE 12

In further experiments, chromium release assays were carried out using the peptides of SEQ ID NOS: 4 and 5, as well as SEQ ID NO: 2. The target cells were allogeneic melanoma cells, i.e., MZ2-MEL, previously transfected with HLA-A2, and cell line T2, which presents HLA-A2, but has an antigen processing defect which results in an increased capacity to present exogenous peptides (Cerundolo et al., Nature 345: 449 (1990)). All cells were pretreated with monoclonal antibody MA2.1 for fifty minutes. The cells were incubated with the peptide of choice, for 30 minutes, at various concentrations. Then, one of CTL clones 210/9 and ISVB was added in an effector: target ratio of 60. Chromium release was measured after four hours, in the manner described supra.

Figure 7A:
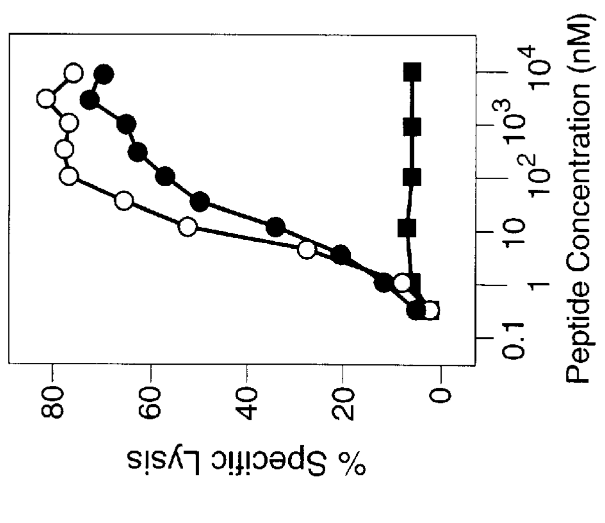
FIGS. 7A and 7D presents experiments where the peptide of SEQ ID NO: 4 was used.
Figure 7B:
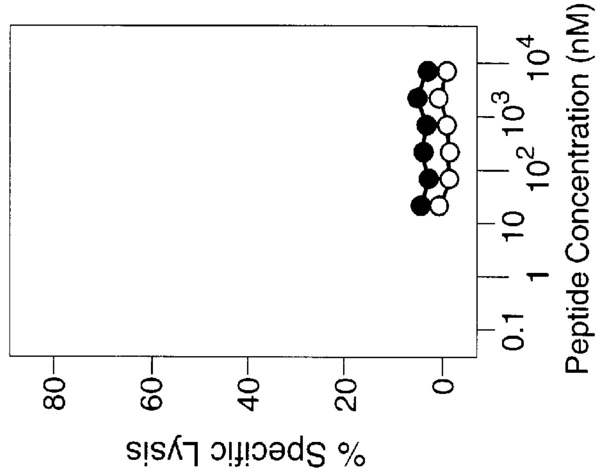
FIGS. 7B and 7E show results where the peptide of SEQ ID NO: 5 was used.
Figure 7C:
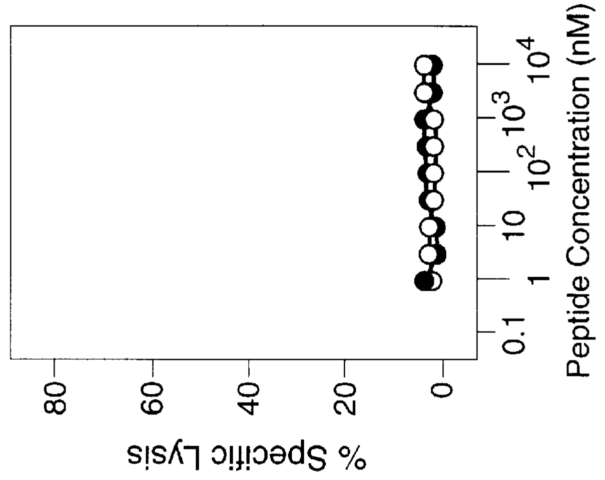
FIGS. 7C and 7F set forth results obtained using SEQ ID NO: 2.
Figure 7D:
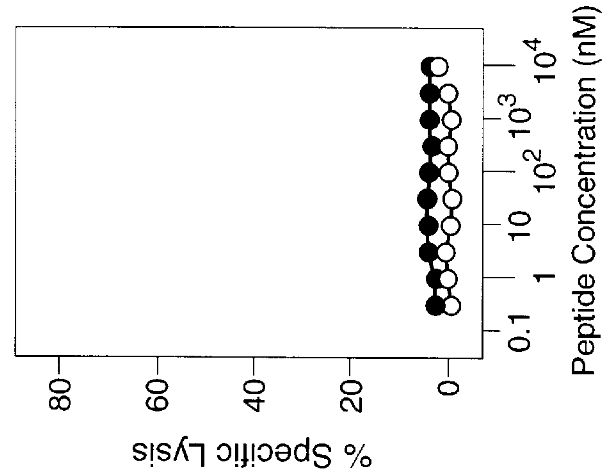
Figure 7E:
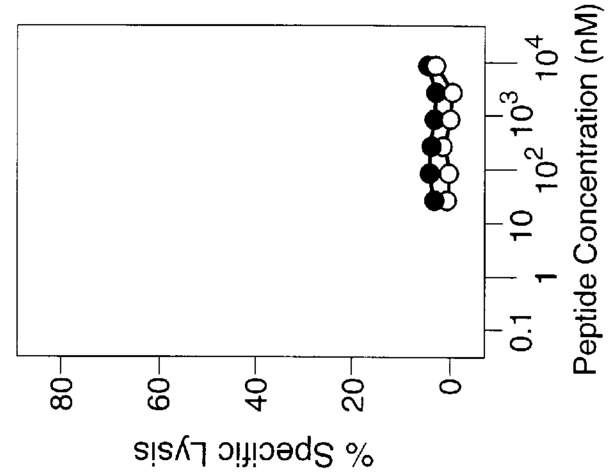
Figure 7F:
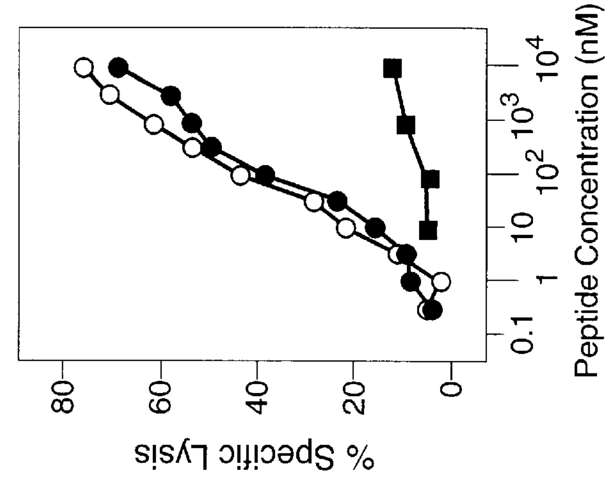

The results are presented in FIG. 7, i.e., FIGS. 7A–7C. The peptide of SEQ ID NO: 4 sensitized cells to CTL 210/9, while SEQ ID NO: 5 did not. SEQ ID NO: 2 sensitized cells to CTL IVSB, as already noted in previous examples.

TABLE 5

| 1 Effecteur | 2 Peptide | 3 Dose | 4 T2 +s-A2 | 5 G22 +s-A2 | 6 G2.2.5+ a-A2 |
|---|---|---|---|---|---|
| DAG | MLLAVLYCLL | 10 μM | | 32 | 3 |
| 210/5 | (LAUS 17-5) | 3 | 45 | 32 | 5 |
| 50:1 | | 1 | 39 | 26 | 3 |
| | | 300 nM | 33 | 18 | 4 |
| | | 100 | 24 | 8 | 5 |
| | | 30 | 13 | 5 | 6 |
| | | 10 | 6 | 5 | 5 |
| | | 3 | 2 | 2 | 4 |
| | | 1 | 2 | 1 | 3 |
| | | 300 pg | 1 | 4 | 3 |
| | MLLAVLYCL | 10 μM | 85 | 65 | 7 |
| | (LAUS 19-5) | 3 | 87 | 60 | 4 |
| | | 1 | 95 | 68 | 5 |
| | | 300 nM | 95 | 60 | 3 |
| | | 100 | 91 | 56 | 3 |
| | | 30 | 87 | 48 | 3 |
| | | 10 | 82 | | 6 |
| | | 3 | 78 | | 4 |
| | | 1 | 76 | | 5 |
| | | 300 pg | 78 | | 5 |
| | LLAVLYCLL | 10 μM | 0 | 1 | 3 |
| | (Laus 19-10) | 3 | 0 | 2 | 4 |
| | | 1 | 3 | 3 | 3 |
| | | 300 mM | 0 | 2 | 4 |
| | | 100 | 1 | 2 | 4 |
| | | 30 | 1 | 1 | 2 |
| | YMNGTMSQV | 10 μM | 4 | 3 | 4 |
| | (MAINZ) | 3 | 4 | 1 | 5 |
| | | 1 | 2 | 2 | 4 |
| | | 300 nM | 1 | 3 | 2 |
| | | 100 | 0 | 1 | 6 |
| | | 30 | 0 | 2 | 4 |
| | | 10 | 0 | | 3 |
| | | 3 | 3 | | 3 |
| | | 1 | 2 | | 5 |
| | 0 | | 0 | 3 | 7 |
| DAG | MLLAVLYCLL | 10 μM | 26 | 23 | 8 |
| 210/3 | (LAUS 17-5) | 3 | 20 | 23 | 6 |
| 60:1 | | 1 | 19 | 22 | 8 |
| | | 300 nM | 13 | 16 | 7 |
| | | 100 | 10 | 0 | 6 |
| | | 30 | 5 | 6 | 7 |
| | | 10 | 3 | 4 | 6 |
| | | 3 | 5 | 9 | 5 |
| | | 1 | 7 | 3 | 6 |
| | | 300 pg | 1 | 4 | 8 |
| | | 100 | 1 | 3 | 8 |
| | | 30 | 1 | 4 | 7 |
| | MLLAVLYCL | 10 μM | 98 | 82 | 12 |
| | (LAUS 19-5) | 3 | 92 | 75 | 10 |
| | | 1 | 89 | 74 | 6 |
| | | 300 nM | 85 | 87 | 6 |
| | | 100 | 87 | 83 | 8 |
| | | 30 | 93 | 53 | 5 |
| | | 10 | 82 | 42 | 9 |
| | | 3 | 87 | 34 | 8 |
| | | 1 | 77 | 30 | 7 |
| | | 300 pg | 70 | 25 | 7 |
| | | 100 | 73 | 27 | 6 |
| | | 30 | 41 | 22 | 6 |
| | LLAVLYCLL | 10 μM | 1 | 3 | 7 |
| | (Laus 19-10) | 3 | 1 | 3 | 8 |
| | | 1 | 4 | 4 | 9 |

| 7 | 8 Effecteur | 9 Peptide | 10 Dose | 11 T2 +s-A2 | 12 G 2.2 +s-A2 | 13 G2.2.5 +s-A2 |
|---|---|---|---|---|---|---|
| | SK29 | MLLAVLYCLL | 10 μM | 3 | 3 | 7 |
| | IVSB | (LAUS 17-5) | 3 | 0 | 2 | 7 |
| | 60:1 | | 1 | 2 | 3 | 4 |
| | | | 300 nM | 3 | 1 | 6 |
| | | | 100 | 1 | 2 | 7 |
| | | | 30 | 1 | 4 | 7 |
| | | | 10 | 0 | 3 | 7 |
| | | | 3 | 2 | 4 | 7 |
| | | | 1 | 2 | 4 | 6 |
| | | | 300 pg | 1 | 4 | 7 |
| | | MLLAVLYCL | 10 μM | 2 | 3 | 6 |
| | | (LAUS 19-5) | 3 | 1 | 4 | 6 |
| | | | 1 | 0 | 4 | 6 |
| | | | 300 nM | 1 | 3 | 7 |
| | | | 100 | 1 | 4 | 6 |
| | | | 30 | 0 | 4 | 6 |
| | | | 10 | 0 | 4 | 6 |
| | | | 3 | 1 | 4 | 6 |
| | | | 1 | 1 | 3 | 3 |
| | | | 300 pg | 0 | 3 | 6 |
| | | LLAVLYCLL | 10 μM | 3 | 6 | 7 |
| | | (Laus 19-10) | 3 | 0 | 3 | 7 |
| | | | 1 | 1 | 3 | 6 |
| | | | 300 nM | 2 | 3 | 6 |
| | | | 100 | 1 | 5 | 5 |
| | | | 30 | 1 | 4 | 10 |
| | | YMNGTMSQV | 10 μM | 78 | 69 | 8 |
| | | (MAINZ) | 3 | 73 | 60 | 4 |
| | | | 1 | 62 | 55 | 7 |
| | | | 300 nM | 58 | 51 | 6 |
| | | | 100 | 46 | 40 | 7 |
| | | | 30 | 30 | 25 | 7 |
| | | | 10 | 23 | 18 | 8 |
| | | | 3 | 13 | 11 | 4 |
| | | | 1 | 3 | 9 | 5 |
| | | | 300 pg | 7 | 7 | 8 |
| | | | 100 | 4 | 7 | 7 |
| | | | 30 | 2 | 7 | 8 |
| | | | 0 | 2 | 3 | 5 |
| | apl. rel. | | | 184 | 441 | 195 |
| | max-spt | | | 1033 | 2522 | 1686 |
| | % | | | 15 | 15 | 10 |

The foregoing experiments demonstrate that tyrosinase is processed as a tumor rejection antigen precursor, leading to formation of complexes of the resulting tumor rejection antigens with a molecule on at least some abnormal cells, for example, melanoma cells with HLA-A2 or HLA-B44 phenotype. The complex can be recognized by CTLs, and the presenting cell lysed. This observation has therapeutic and diagnostic ramifications which are features of the invention. With respect to therapies, the observation that CTLs which are specific for abnormal cells presenting the aforementioned complexes are produced, suggests various therapeutic approaches. One such approach is the administration of CTLs specific to the complex to a subject with abnormal cells of the phenotype at issue. It is within the skill of the artisan to develop such CTLs in vitro. Specifically, a sample of cells, such as blood cells, are contacted to a cell presenting the complex and are capable of provoking a specific CTL to proliferate. The target cell can be a transfectant, such as a COS cell of the type described supra. These transfectants present the desired complex on their surface and, when combined with a CTL of interest, stimulate its proliferation. So as to enable the artisan to produce these CTLs, vectors containing the genes of interest, i.e., pcDNA-1/Amp1 (HLA-A2), and p123.B2 (human tyrosinase), have been deposited in accordance with the Budapest Treaty at the Institut Pasteur, under Accession Numbers I1275 and I1276, respectively. COS cells, such as those used herein are widely available, as are other suitable host cells.

To detail the therapeutic methodology, referred to as adoptive transfer (Greenberg, J. Immunol. 136(5): 1917 (1986); Reddel et al., Science 257: 238 (7-10-92); Lynch et al., Eur. J. Immunol. 21: 1403–1410 (1991); Kast et al., Cell 59: 603–614 (11-17-89) ), cells presenting the desired complex are combined with CTLs leading to proliferation of the CTLs specific thereto. The proliferated CTLs are then administered to a subject with a cellular abnormality which is characterized by certain of the abnormal cells presenting the particular complex. The CTLs then lyse the abnormal cells, thereby achieving the desired therapeutic goal.

The foregoing therapy assumes that at least some of the subject's abnormal cells present one or more of the HLA/tyrosinase derived peptide complexes. This can be determined very easily. For example CTLs are identified using the transfectants discussed supra, and once isolated, can be used with a sample of a subject's abnormal cells to determine lysis in vitro. If lysis is observed, then the use of specific CTLs in such a therapy may alleviate the condition associated with the abnormal cells. A less involved methodology examines the abnormal cells for their HLA phenotype, using standard assays, and determines expression of tyrosinase via amplification using, e.g., PCR. The fact that a plurality of different HLA molecules present TRAs derived from tyrosinase increases the number of individuals who are suitable subjects for the therapies discussed herein.

Adoptive transfer is not the only form of therapy that is available in accordance with the invention. CTLs can also be provoked in vivo, using a number of approaches. One approach, i.e., the use of non-proliferative cells expressing the complex, has been elaborated upon supra. The cells used in this approach may be those that normally express the complex, such as irradiated melanoma cells or cells transfected with one or both of the genes necessary for presentation of the complex. Chen et al., Proc. Natl. Acad. Sci. USA 88: 110–114 (January, 1991) exemplifies this approach, showing the use of transfected cells expressing HPVE7 peptides in a therapeutic regime. Various cell types may be used. Similarly, vectors carrying one or both of the genes of interest may be used. Viral or bacterial vectors are especially preferred. In these systems, the gene of interest is carried by, e.g., a Vaccinia virus or the bacteria BCG, and the materials de facto "infect" host cells. The cells which result present the complex of interest, and are recognized by autologous CTLs, which then proliferate. A similar effect can be achieved by combining tyrosinase itself with an adjuvant to facilitate incorporation into HLA-A2 presenting cells. The enzyme is then processed to yield the peptide partner of the HLA molecule.

The foregoing discussion refers to "abnormal cells" and "cellular abnormalities". These terms are employed in their broadest interpretation, and refer to any situation where the cells in question exhibit at least one property which indicates that they differ from normal cells of their specific type. Examples of abnormal properties include morphological and biochemical changes, e.g. Cellular abnormalities include tumors, such as melanoma, autoimmune disorders, and so forth.

The invention also provides a method for identifying precursors to CTL targets. These precursors are referred to as tumor rejection antigens when the target cells are tumors, but it must be pointed out that when the cell characterized by abnormality is not a tumor, it would be somewhat misleading to refer to the molecule as a tumor rejection antigen. Essentially, the method involves identifying a cell which is the target of a cytolytic T cell of the type discussed supra. Once such a cell is identified, total RNA is converted to a cDNA library, which is then transfected into a cell sample capable of presenting an antigen which forms a complex with a relevant HLA molecule. The transfectants are contacted with the CTL discussed supra, and again, targeting by the CTL is observed (lysis and/or TNF production). These transfectants which are lysed are then treated to have the cDNA removed and sequenced, and in this manner a precursor for an abnormal condition, such as a tumor rejection antigen precursor, can be identified.

Other aspects of the invention will be clear to the skilled artisan and need not be repeated here.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. A method for identifying a subject for treatment with a therapeutic agent which is specific for complexes of an HLA molecule and a tyrosinase derived peptide consisting of the amino acid sequence of SEQ ID NO: 4, wherein said complexes are present on surfaces of abnormal cells of said subject, comprising:
    (i) contacting a sample containing abnormal cells, which has been taken from said subject, with a cytolytic T cell specific of said complexes,
    (ii) determining lysis of at least some of said abnormal cells as an indication that the subject is a candidate for said treatment.

2. Isolated cytolytic T cell specific for a complex of HLA-A2 and the tyrosinase derived peptide consisting of the amino acid sequence of SEQ ID NO: 4.

3. A method for identifying abnormal cells which present complexes of an HLA molecule and a tyrosinase derived peptide consisting of the amino acid of SEQ ID NO: 4 on their surfaces, comprising contacting a sample which contains said abnormal cells with a cytolytic T cell specific for said complexes and determining lysis of said abnormal cells by said cytolytic T cells as a determination of said abnormal cells.

* * * * *

SEQUENCE LISTING ( 1 ) GENERAL INFORMATION:

( i i i ) NUMBER OF SEQUENCES: 5

( 2 ) INFORMATION FOR SEQ ID NO: 1:

( i ) SEQUENCE CHARACTERISTICS:
( A ) LENGTH: 1894 base pairs
( B ) TYPE: nucleic acid
( C ) STRANDEDNESS: single
( D ) TOPOLOGY: linear ( x i ) SEQUENCE DESCRIPTION: SEQ ID NO: 1:

GGA AGA ATG CTC CTG GCT GTT TTG TAC TGC CTG CTG TGG AGT TTC CAG 48
Gly Arg Met Leu Leu Ala Val Leu Tyr Cys Leu Leu Trp Ser Phe Gln
-15 -10 -5

ACC TCC GCT GGC CAT TTC CCT AGA GCC TGT GTC TCC TCT AAG AAC CTG 96
Thr Ser Ala Gly His Phe Pro Arg Ala Cys Val Ser Ser Lys Asn Leu
1 5 10

ATG GAG AAG GAA TGC TGT CCA CCG TGG AGC GGG GAC AGG AGT CCC TGT 144
Met Gly Lys Glu Cys Cys Pro Pro Trp Ser Gly Asp Arg Ser Pro Cys
15 20 25 30

GGC CAG CTT TCA GGC AGA GGT TCC TGT CAG AAT ATC CTT CTG TCC AAT 192
Gly Gln Leu Ser Gly Arg Gly Ser Cys Gln Asn Ile Leu Leu Ser Asn
35 40 45

GCA CCA CTT GGG CCT CAA TTT CCC TTC ACA GGG GTG GAT GAC CGG GAG 240
Ala Pro Leu Gly Pro Gln Phe Pro Phe Thr Gly Val Asp Asp Arg Glu
50 55 60

TCG TGG CCT TCC GTC TTT TAT AAT AGG ACC TGC CAG TGC TCT GGC AAC 288
Ser Trp Pro Ser Val Phe Tyr Asn Arg Thr Cys Gln Cys Ser Gly Asn
65 70 75

TTC ATG GGA TTC AAC TGT GGA AAC TGC AAG TTT GGC TTT TGG GGA CCA 336
Phe Met Gly Phe Asn Cys Gly Asn Cys Lys Phe Gly Phe Trp Gly Pro
80 85 90

AAC TGC ACA GAG AGA CGA CTC TTG GTG AGA AGA AAC ATC TTC GAT TTG 384
Asn Cys Thr Glu Arg Arg Leu Leu Val Arg Arg Asn Ile Phe Asp Leu
95 100 105 110

AGT GCC CCA GAG AAG GAC AAA TTT TTT GCC TAC CTC ACT TTA GCA AAG 432
Ser Ala Pro Glu Lys Asp Lys Phe Phe Ala Tyr Leu Thr Leu Ala Lys
115 120 125

CAT ACC ATC AGC TCA GAC TAT GTC ATC CCC ATA GGG ACC TAT GGC CAA 480
His Thr Ile Ser Ser Asp Tyr Val Ile Pro Ile Gly Thr Tyr Gly Gln
130 135 140

ATG AAA AAT GGA TCA ACA CCC ATG TTT AAC GAC ATC AAT ATT TAT GAC 528
Met Lys Asn Gly Ser Thr Pro Met Phe Asn Asp Ile Asn Ile Tyr Asp
145 150 155

CTC TTT GTC TGG ATG CAT TAT TAT GTG TCA ATG GAT GCA CTG CTT GGG 576
Leu Phe Val Trp Ile His Tyr Tyr Val Ser Met Asp Ala Leu Leu Gly
160 165 170

GGA TCT GAA ATC TGG AGA GAC ATT GAT TTT GCC CAT GAA GCA CCA GCT 624
Gly Tyr Glu Ile Trp Arg Asp Ile Asp Phe Ala His Glu Ala Pro Ala
175 180 185 190

TTT CTG CCT TGG CAT AGA CTC TTC TTG TTG CGG TGG GAA CAA GAA ATC 672
Phe Leu Pro Trp His Arg Leu Phe Leu Leu Arg Trp Glu Gln Gly Ile
195 200 205

CAG AAG CTG ACA GGA GAT GAA AAC TTC ACT ATT CCA TAT TGG GAC TGG 720
Gln Lys Leu Thr Gly Asp Gly Asn Phe Thr Ile Pro Tyr Trp Asp Trp
210 215 220

CGG GAT GCA GAA AAG TGT GAC ATT TGC ACA GAT GAG TAC ATG GGA GGT 768
Arg Asp Ala Glu Lys Cys Asp Ile Cys Thr Asp Gly Tyr Met Gly Gly

-continued 225 230 235

CAG CAC CCC ACA AAT CCT AAC TTA CTC AGC CCA GCA TCA TTC TTC TCC 816
Gln His Pro Thr Asn Pro Asn Leu Leu Ser Pro Ala Ser Phe Phe Ser
240 245 250

TCT TGG CAG ATT GTC TGT AGC CGA TTG GAG GAG TAC AAC AGC CAT CAG 864
Ser Trp Gln Ile Val Cys Ser Arg Leu Glu Glu Tyr Asn Ser His Gln
255 260 265 270

TCT TTA TGC AAT GGA ACG CCC GAG GGA CCT TTA CGG CGT AAT CCT GGA 912
Ser Leu Cys Asn Gly Thr Pro Glu Gly Pro Leu Arg Arg Asn Pro Gly
275 280 285

AAC CAT GAC AAA TCC AGA ACC CCA AGG CTC CCC TCT TCA GCT GAT GTA 960
Asn His Asp Lys Ser Arg Thr Pro Arg Leu Pro Ser Ser Ala Asp Val
290 295 300

GAA TTT TGC CTG AGT TTG ACC CAA TAT GAA TCT GGT TCC ATG GAT AAA 1008
Glu Phe Cys Leu Ser Leu Thr Gln Tyr Glu Ser Gly Ser Met Asp Lys
305 310 315

GCT GCC AAT TTC AGC TTT AGA AAT ACA CTG GAA GGA TTT GCT AGT CCA 1056
Ala Ala Asn Phe Ser Phe Arg Asn Thr Leu Glu Gly Phe Als Ser Pro
320 325 330

CTT ACT GGG ATA GCG GAT GCC TCT CAA AGC AGC ATG CAC AAT GCC TTG 1104
Leu Thr Gly Ile Ala Asp Ala Ser Gln Ser Ser Met His Asn Ala Leu
335 340 345 350

CAC ATC TAT ATG AAT GGA ACA ATG TCC CAG GTA CAG GGA TCT GCC AAC 1152
His Ile Tyr Met Asn Gly Thr Met Ser Gln Met Gln Gly Ser Ala Asn
355 360 365

GAT CCT ATC TTC CTT CTT CAC CAT GCA TTT GTT GAC AGT ATT TTT GAG 1200
Asp Pro Ile Phe Leu Leu His His Ala Phe Val Asp Ser Ile Phe Glu
370 375 380

CAG TGG CTC CAA AGG CAC CGT CCT CTT CAA GAA GTT TAT CCA GAA GCC 1248
Gln Trp Leu Arg Arg His Arg Pro Leu Gln Glu Val Tyr Pro Glu Ala
385 390 395

AAT GCA CCC ATT GGA CAT AAC CGG GAA TCC TAC ATG GTT CCT TTT ATA 1296
Asn Ala Pro Ile Gly His Asn Arg Glu Ser Tyr Met Val Pro Phe Ile
400 405 410

CCA CTG TAC AGA AAT GGT GAT TTC TTT ATT TCA TCC AAA GAT CTG GGC 1344
Pro Leu Tyr Arg Asn Gly Asp Phe Phe Ile Ser Ser Lys Asp Leu Gly
415 420 425 430

TAT GAC TAT AGC TAT CTA CAA GAT TCA GAC CCA GAC TCT TTT CAA GAC 1392
Tyr Asp Tyr Ser Tyr Leu Gln Asp Ser Asp Pro Asp Ser Phe Gln Asp
435 440 445

TAC ATT AAG TCC TAT TTG GAA CAA GCG AGT CGG ATC TGG TCA TGG CTC 1440
Tyr Ile Lys Ser Tyr Leu Gly Gln Ala Ser Arg Ile Trp Ser Trp Leu
450 455 460

CTT GGG GCG GCG ATG GTA GGG GCC GTC CTC ACT GCC CTG CTG GCA GGG 1488
Leu Gly Ala Ala Met Val Gly Ala Val Leu Thr Ala Leu Leu Ala Gly
465 470 475

CTT GTG AGC TTG CTG TGT CGT CAC AAG AGA AAG CAG CTT CCT GAA GAA 1536
Leu Val Ser Leu Leu Cys Arg His Lys Arg Lys Gln Leu Pro Glu Glu
480 485 490

AAG CAG CCA CTC CTC ATG GAG AAA GAG GAT TAC CAC AGC TTG TAT CAG 1584
Lys Gln Pro Leu Leu Met Glu Lys Glu Asp Tyr His Ser Leu Tyr Gln
495 500 505 510

AGC CAT TTA 1593
Ser His Leu
513

TAAAAGGCTT AGGCAATAGA GTAGGGCCAA AAAGCCTGAC CTCACTCTAA CTCAAAGTAA 1653

TGTCCAGGTT CCCAGAGAAT ATCTGCTGGT ATTTTTCTGT AAAGACCATT TGCAAAATTG 1713

TAACCTAATA CAAAGTGTAG CCTTCTTCCA ACTCAGGTAG AACACACCTG TCTTTGTCTT 1773

-continued

| | | | | | |
|---|---|---|---|---|---|
| GCTGTTTTCA | CTCAGCCCTT | TTAACATTTT | CCCCTAAGCC | CATATGTCTA | AGGAAAGGAT | 1833 |
| GCTATTTGGT | AATGAGGAAC | TGTTATTTGT | ATGTGAATTA | AAGTGCTCTT | ATTTTAAAAA | 1893 |
| A | | | | | | 1894 |

( 2 ) INFORMATION FOR SEQ ID NO: 2:

( i ) SEQUENCE CHARACTERISTICS:
        ( A ) LENGTH: 9 amino acid residues
        ( B ) TYPE: amino acid
        ( D ) TOPOLOGY: linear ( x i ) SEQUENCE DESCRIPTION: SEQ ID NO: 2:

Tyr Met Asn Gly Thr Met Ser Gln Val
            5

( 2 ) INFORMATION FOR SEQ ID NO: 3:

( i ) SEQUENCE CHARACTERISTICS:
        ( A ) LENGTH: 10 amino acid residues
        ( B ) TYPE: amino acid
        ( D ) TOPOLOGY: linear ( x i ) SEQUENCE DESCRIPTION: SEQ ID NO: 3:

Met Leu Leu Ala Val Leu Tyr Cys Leu Leu
           5                   10

( 2 ) INFORMATION FOR SEQ ID NO: 4:

( i ) SEQUENCE CHARACTERISTICS:
        ( A ) LENGTH: 9 amino acid residues
        ( B ) TYPE: amino acid
        ( D ) TOPOLOGY: linear ( x i ) SEQUENCE DESCRIPTION: SEQ ID NO: 4:

Met Leu Leu Ala Val Leu Tyr Cys Leu
            5

( 2 ) INFORMATION FOR SEQ ID NO: 5:

( i ) SEQUENCE CHARACTERISTICS:
        ( A ) LENGTH: 9 amino acid residues
        ( B ) TYPE: amino acid
        ( D ) TOPOLOGY: linear ( x i ) SEQUENCE DESCRIPTION: SEQ ID NO: 5:

Leu Leu Ala Val Leu Tyr Cys Leu Leu
            5